US008036861B2

(12) United States Patent
Rimsky et al.

(10) Patent No.: US 8,036,861 B2
(45) Date of Patent: Oct. 11, 2011

(54) METHOD AND MEANS FOR DETERMINING THE REPLICATION RATE OF A VIRAL POPULATION

(75) Inventors: Laurence Tatiana Rimsky, Kapellen (BE); Herwig Gaston Emiel Van Marck, Eke (BE); Marie-Pierre T. M. M. G. De Bethune, Everberg (BE); Lee Terry Bacheler, Chapel Hill, NC (US)

(73) Assignee: Tibotec Pharmaceuticals, Little Island, County Cork (IE)

( * ) Notice: Subject to any disclaimer, the term of this patent is extended or adjusted under 35 U.S.C. 154(b) by 461 days.

(21) Appl. No.: 12/089,249

(22) PCT Filed: Oct. 13, 2006

(86) PCT No.: PCT/EP2006/067383
§ 371 (c)(1),
(2), (4) Date: Apr. 4, 2008

(87) PCT Pub. No.: WO2007/042568
PCT Pub. Date: Apr. 19, 2007

(65) Prior Publication Data
US 2008/0220412 A1 Sep. 11, 2008

Related U.S. Application Data

(60) Provisional application No. 60/727,156, filed on Oct. 14, 2005.

(30) Foreign Application Priority Data

Jan. 20, 2006 (EP) .................................... 06100684
Apr. 14, 2006 (EP) .................................... 06112674

(51) Int. Cl.
*G06F 17/10* (2006.01)
(52) U.S. Cl. .................. 703/2; 703/11; 702/19; 702/23; 435/5
(58) Field of Classification Search ......................... None
See application file for complete search history.

(56) References Cited

FOREIGN PATENT DOCUMENTS

WO WO 2004/003513 A2 1/2004
WO WO 2005/070120 A2 1/2005

OTHER PUBLICATIONS

Blaak, H., et al. "Hiv-2-Infected Individuals With undetectabale Plasma Viremia Carry Replication-Competent Virus in Peripheral Blood Lymphocytes", J. Acquired Immune Defic. Syndr. vol. 36, 3, 2004, pp. 777-782.
Campbell, T., et al. "Relationship between in Vitro Human Immunodeficiency Virus Type 1 Replication Rate and Virus Load in Plasma", Journal of Virology, 2003, pp. 12105-12112.
Diallo, K., et al. "Molecular Impact of the M184V Mutation in Human Immunodeficiency Virus Type 1 Reverse Transcriptase", Antimicrobial Agents and Chemotherapy, 2003, pp. 3377-3383.
Easterbrook, P., et al. "Chemokine Receptor Polymorphisms and Human Immunodeficiency Virus Disease Progression", Journal of Infectious Diseases 1999, p. 1096-105.
Goding, J., "Antibody Production by Hybridomas", Journal of Immunological Methods, 39, 1980, pp. 285-308.
Ham, R. Clonal Growth of Mammalian Cells in a Chemically Defined, Synthetic Medium, Microbiology, 1964, pp. 288-293.
Lucas, S., "The Pathology of HIV Infection", Lepr. Rev., 2002 73, 64-71.
Moore, G., et al. "Culture of Normal Human Leukoctes", JAMA, vol. 199, No. 8, 1967, pp. 87-92.
Morton, H., "A Survey of Commercially Available Tissue Culture Media", National Research Council of Canada, In Vitro, vol. 6, No. 2, 1970, pp. 89-108.
Russell, W., et al. "Factors Affecting Mutagenicity of Ethylnitrosourea in the Mouse Specific-Locus Test and Their Bearing on Risk Estimation", Proceedings of the Third International Conference on Environmental Mutagens (1982), 12 pages.
Russell, W., et al. "Specific-Locus Test Shows Ethylnitrosourea to be the Most Potent Mutagen in the Mouse", Proc. Natl. Acad. Sci. USA vol. 76, No. 11, pp. 5818-5819.
Quinones-Mateu, M., et al. "Dual Infection/Competition Assay Shows a Correlation Between Ex vivo Human Immunodeficiency Virus Type 1 Fitness and Disease Progression", Journal of Virology, 2000, pp. 9222-9233.
Sambrook, J., et al. Commonly Used Techniques, References to Molecular Biology "Techniques", Current Protocols in Human Genetics (1998), 2 pages.
Sarkar, G., et al. "The "Megaprimer" Method of Site-Directed Mutagenesis", Biotechniques, 8(4):404-7 1990.
Blaak, H., et al., "In Vitro Replication Kinetics of Human Immunodeficiency Virus Type 1 (Hiv-1) Variants in Relation to Virus Load in Long-Term Survivors of Hiv-1 Infection," *Journal of Infectious Diseases*, 1998, 177:600-610.
Fiebig, E., et al., "Dynamics of HIV viremia and antibody seroconversion in plasma donors: implications for diagnosis and staging of primary HIV infection," *AIDS*, 2003, 17:1871-1879.

*Primary Examiner* — Carolyn L. Smith
(74) *Attorney, Agent, or Firm* — Patton Boggs LLP

(57) ABSTRACT

The present invention relates to methods and means for determining the replication rate of a viral population. More specifically, the invention provides methods and means for determining the replication rate of a viral population by performing a linear regression on signal data generated by cells infected with dilutions of the viral population. The methods are useful for monitoring the progression of diseases associated with viruses, identifying effective drug regimens for the treatment of viral infections, and identifying and determining the biological effectiveness of potential therapeutic compounds.

12 Claims, 8 Drawing Sheets

Figure 1

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| A | | | IIIB 1/4 | | V1 1/4 | | V2 1/4 | | V3 1/4 | | V4 1/4 | | V5 1/4 | | V6 1/4 | | V7 1/4 | | V8 1/4 | | V9 1/4 | | | medium control |
| B | | | | | | | | | | | | | | | | | | | | | | | | |
| C | | | IIIB 1/8 | | V1 1/8 | | V2 1/8 | | V3 1/8 | | V4 1/8 | | V5 1/8 | | V6 1/8 | | V7 1/8 | | V8 1/8 | | V9 1/8 | | | |
| D | | | | | | | | | | | | | | | | | | | | | | | | |
| E | | | IIIB 1/16 | | V1 1/16 | | V2 1/16 | | V3 1/16 | | V4 1/16 | | V5 1/16 | | V6 1/16 | | V7 1/16 | | V8 1/16 | | V9 1/16 | | | |
| F | | Cell control | | | | | | | | | | | | | | | | | | | | | | |
| G | | | IIIB 1/32 | | V1 1/32 | | V2 1/32 | | V3 1/32 | | V4 1/32 | | V5 1/32 | | V6 1/32 | | V7 1/32 | | V8 1/32 | | V9 1/32 | | | |
| H | | | | | | | | | | | | | | | | | | | | | | | | |
| I | | | IIIB 1/64 | | V1 1/64 | | V2 1/64 | | V3 1/64 | | V4 1/64 | | V5 1/64 | | V6 1/64 | | V7 1/64 | | V8 1/64 | | V9 1/64 | | | Cell control |
| J | | | | | | | | | | | | | | | | | | | | | | | | |
| K | | | IIIB 1/128 | | V1 1/128 | | V2 1/128 | | V3 1/128 | | V4 1/128 | | V5 1/128 | | V6 1/128 | | V7 1/128 | | V8 1/128 | | V9 1/128 | | | |
| L | | | | | | | | | | | | | | | | | | | | | | | | |
| M | | | IIIB 1/256 | | V1 1/256 | | V2 1/256 | | V3 1/256 | | V4 1/256 | | V5 1/256 | | V6 1/256 | | V7 1/256 | | V8 1/256 | | V9 1/256 | | | |
| N | | | | | | | | | | | | | | | | | | | | | | | | |
| O | | | IIIB 1/512 | | V1 1/512 | | V2 1/512 | | V3 1/512 | | V4 1/512 | | V5 1/512 | | V6 1/512 | | V7 1/512 | | V8 1/512 | | V9 1/512 | | | |
| P | | | | | | | | | | | | | | | | | | | | | | | | |

METHOD AND MEANS FOR DETERMINING THE REPLICATION RATE OF A VIRAL POPULATION

CROSS REFERENCE TO RELATED APPLICATIONS

This application claims priority of the benefits of the filing of Patent Application Nos. PCT/EP2006/067383 filed Oct. 13, 2006; EP 06100684.7 filed Jan. 20, 2006; EP 06112674.4 filed Apr. 14, 2006; and U.S. Ser. No. 60/727,156 filed Oct. 14, 2005. The complete disclosures of the aforementioned related applications are hereby incorporated herein by reference for all purposes.

FIELD OF THE INVENTION

The present invention relates to methods and means for determining the replication rate of a viral population. The methods and means are useful for monitoring the progression of diseases associated with viruses, identifying effective drug regimens for the treatment of viral infections, and identifying and determining the biological effectiveness of potential therapeutic compounds.

BACKGROUND OF THE INVENTION

More than 60 million people have been infected with the human immunodeficiency virus (HIV), the causative agent of acquired immune deficiency syndrome (AIDS), since the early 1980s. See Lucas, 2002, Lepr Rev. 73(1):64-71. HIV/AIDS is now the leading cause of death in sub-Saharan Africa, and is the fourth biggest killer worldwide. At the end of 2004, an estimated 39.4 million people were living with HIV globally, and still newly infected people with HIV is amounting to 4.9 million at the end of 2004 (source: UNAIDS).

Antiviral therapy targets different stages of the HIV life cycle and a variety of enzymes essential for HIV's replication and/or survival. Amongst the drugs that have so far been approved for AIDS therapy are nucleoside reverse transcriptase inhibitors (NRTI) such as AZT, ddI, ddC, d4T, 3TC, abacavir, non-nucleoside reverse transcriptase inhibitors (NNRTI) such as nevirapine, efavirenz, delavirdine, protease inhibitors such as saquinavir, ritonavir, indinavir, nelfinavir, amprenavir and lopinavir, entry inhibitors, etc.

In the absence of antiviral therapy, most HIV-1-infected individuals progress to AIDS and death. The median time between seroconversion and the development of AIDS is approximately 10 years (Easterbrook, 1999. J. Infect.). Rates of disease progression, however, are highly variable, ranging from rapid progression to AIDS within 1 year to long-term asymptomatic survival for over 15 years.

Several lines of evidence support an association between viral phenotype and rate of HIV-1 disease progression. Long-term non-progressors who harbor HIV-1 with mutations in nef have been described, and the viruses infecting those individuals have been characterized as less fit than wild-type viruses from individuals with progressive disease (Blaak et al. 1998. J. Infect. Dis.). Assays that measure the contribution of reverse transcriptase (RT) and protease (PR) to virus replication have been used to show that drug-resistant HIV-1 isolates have impaired replicative capacity. For instance, in Diallo et al. (Antimic. Agents and Chem., 2003) it is reported that a M184V substitution in HIV-1 reverse transcriptase, encoding high-level resistance to lamivudine (3TC), results in decreased HIV-1 replicative capacity, diminished RT processivity, and increased RT fidelity in biochemical assays.

In addition, diminished fitness of these isolates has been hypothesized to explain the clinical benefit of antiretroviral therapy in the setting of persistent virus replication. Further evidence for a link between virus replication rate and disease progression is suggested by the results of a study that showed that HIV-1 harbored by three long-term survivors had significantly less replicative fitness in growth competition experiments compared with HIV-1 harbored by three individuals with progressive disease (Quinones-Mateu, et al. 2000. J. Virol.). Campbell et al. (2003, J. Virol.) concluded that differences in HIV-1 replication rates among HIV-1 isolates are a major determinant of disease progression. As such, changes in the replication rate of a virus are of major clinical importance because they can affect the response of a patient to antiviral therapies, and are indicative of disease progression.

Fiebig Eberhard W. et al. in "Dynamics of HIV viremia and antibody seroconversion in plasma donors: implications for diagnosis and staging of primary HIV infection" AIDS (Hagerstown) vol. 17, no. 13, 2003, concludes that the quantitative analysis of preseroconversion replication rates of HIV is useful for projecting the yield and predictive value of assays targeting primary HIV infection.

WO04/003513 provides a method for determining the replication capacity of HIV. The method is based on an analysis of a panel of recombinant virus vectors created using site-directed mutagenesis containing one or more reverse transcriptase (RT) amino acid substitutions. The method basically detects whether the RT encoded by a HIV exhibits the presence or absence of a mutation associated with impaired replication capacity at amino acid position 98, 100, 101, 103, 106, 108, 179, 181, 188, 190, 225 or 236 of the amino acid sequence of said reverse transcriptase, wherein the presence of said mutation indicates that the HIV has an increased likelihood of having impaired replication capacity.

The method described in WO04/003513 thus relies on the knowledge of pre-existing data which associates specific RT mutations with a given replication capacity. Such method is thus not able to determine the replication rate of a diverse viral population encompassing other RT mutations, let alone protease mutations or any other enzymatic changes.

Campbell et al. (2003, J. Virol.) disclose a method for determining HIV-1 replication rates, said method encompassing the steps of culturing autologous virus isolates in phytohemagglutinin-treated peripheral blood mononuclear cells (PBMC), and determining the rate of p24 antigen production during its phase of exponential increase by fitting by linear regression, whereby the slope of the regression is the viral replication rate. Campbell et al. provide as well a method for determining the RT and PR replication capacity in a single cycle-based assay using recombinant virus that contain the RT and PR genes of each HIV-1 isolate. The replication capacity is the percentage of virus replication relative to the reference virus strain, NL4-3.

There is still an unresolved problem when determining the replication rate of viral stock of unknown titer. The titer of a viral population indicates the strength or potency of said viral population in infecting cells. The titer of a specific viral population can be defined as the highest dilution of said viral population giving a cytopathogenic effect (CPE) in 50% of inoculated cell cultures. Viral stocks which have a much too high or a much too low titer are usually difficult to measure because the indicator signals thereof fall out of the limits of detection of the analytical instrument used in said methodologies.

There is thus a need for a method for determining the replication rate of a viral population of unknown titer.

There is also a need for a method for determining the replication rate of a viral population which is not limited to specific mutant strains exhibiting specific RT mutations.

There is as well a need for a method for determining the replication rate of a viral population which is standardized, which can mimic an in vivo setting, is easy to use and easy to quantify in a precise manner. Importantly, there is the need of a superior method in terms of accuracy for determining the replication rate of a viral population.

It is an object of the invention to provide a method for determining the replication rate of a viral population with an unknown viral titer.

It is an object of the invention to provide a method for determining the replication rate of a viral population consisting of different viral types, strains, and quasispecies, and is further not limited to specific mutant strains.

It is an object of the invention to provide a method for determining the replication rate of a viral population which does not need to employ primers, probes, or any other analytical compounds designed and validated for each virus studied.

It is an object of the invention to provide a model for determining the replication rate of a viral population which can mimic in vivo conditions, is easy to use and easy to quantify in a precise manner.

It is an object of the invention to provide a method for determining the replication rate of a viral population which is accurate in estimating the replication rate.

It is an object of the invention to provide a method for determining the replication rate of a viral population which tests the complete full cycle of replication thereof.

It is an object of the invention to provide a method for determining the replication rate of a viral population in any chosen environment.

SUMMARY OF THE INVENTION

The present invention relates to a method for the determination of the replication rate of a viral population, said method comprising the steps of:
a) diluting the viral population into at least 2 different dilutions;
b) providing cells into wells, wherein the amount of wells is the amount of the different dilutions from step a) in duplicate, triplicate or any other multiple;
c) infecting the multiple wells of cells with each dilution of the viral population so as to promote the replication of said viral population, wherein said cells or viral population comprise a phenotypic marker, whose signal is proportional to the logarithm of the viral population count;
d) measuring in a suitable device for each well the signal expressed by the phenotypic marker at least 2 different time points;
e) calculating a weight (w) for each group of signals of the wells with the same dilution at each time point (dilution multiple set), whereby said weight is a monotone decreasing function of the standard deviation of the signals;
f) plotting the logarithm of the signal data obtained from step d), in function of the time, and disregarding the signal data which is outside the linear region;
g) extrapolating each remaining signal data by adding said each remaining signal data to the logarithm of each dilution factor at which the viral population was diluted;
h) calculating the replication rate by performing a linear regression on the extrapolated remaining signal data and their corresponding time points; wherein the replication rate of the viral population (RR) is calculated according to the formula:

$$RR = \frac{\sum_{i=1}^{n} w_i x_i y_i - \frac{\sum_{i=1}^{n} w_i x_i \sum_{i=1}^{n} w_i y_i}{\sum_{i=1}^{n} w_i}}{\sum_{i=1}^{n} w_i x_i^2 - \frac{\left(\sum_{i=1}^{n} w_i x_i\right)^2}{\sum_{i=1}^{n} w_i}},$$

wherein "w" is the weight for each signal data set, "x" is a time point, "y" is each signal data for a given time point multiplied by the dilution factor, and "n" is the total number of signal data.

The method for measuring replication rate can be adapted to a variety of viruses, including, but not limited to retroviruses, e.g. HIV, murine leukemia virus, polyoviruses, e.g. polyoma, and herpesviruses (e.g. human cytomegalovirus).

The invention further relates to a method for using replication rate measurements to guide the treatment of HIV-1, for example, to methods for using replication rate measurements to guide the treatment of patients failing antiretroviral drug treatment or for using replication rate measurements to guide the treatment of patients newly infected with HIV-1. The methods for using replication rate measurements to guide the treatment of HIV-1 can be adapted to other viruses, including, but not limited to murine leukemia virus, polyoviruses, e.g. polyoma, and herpesviruses (e.g. human cytomegalovirus).

The methods of the invention significantly improve the quality of life of a patient by providing information to the clinician useful for the design of more effective antiviral treatment regimens. Also, by avoiding the administration of ineffective drugs, considerable time and money is saved.

The methods of the invention provide in addition a computer-based system for the determination of the replication rate of a viral population.

The methods of the invention further provide a diagnostic system for determining the replication rate of a viral population, said diagnostic system comprising means for diluting a viral population; means for providing cells into wells; means for infecting cells so as to promote the replication of said viral population; means for measuring the signal expressed by the phenotypic marker; and means for calculating the replication rate.

BRIEF DESCRIPTION OF THE FIGURES

FIG. 1 shows a 384-well plate filled with dilutions of different virus in quadruplicates.

DESCRIPTION OF THE INVENTION

Figure 2:
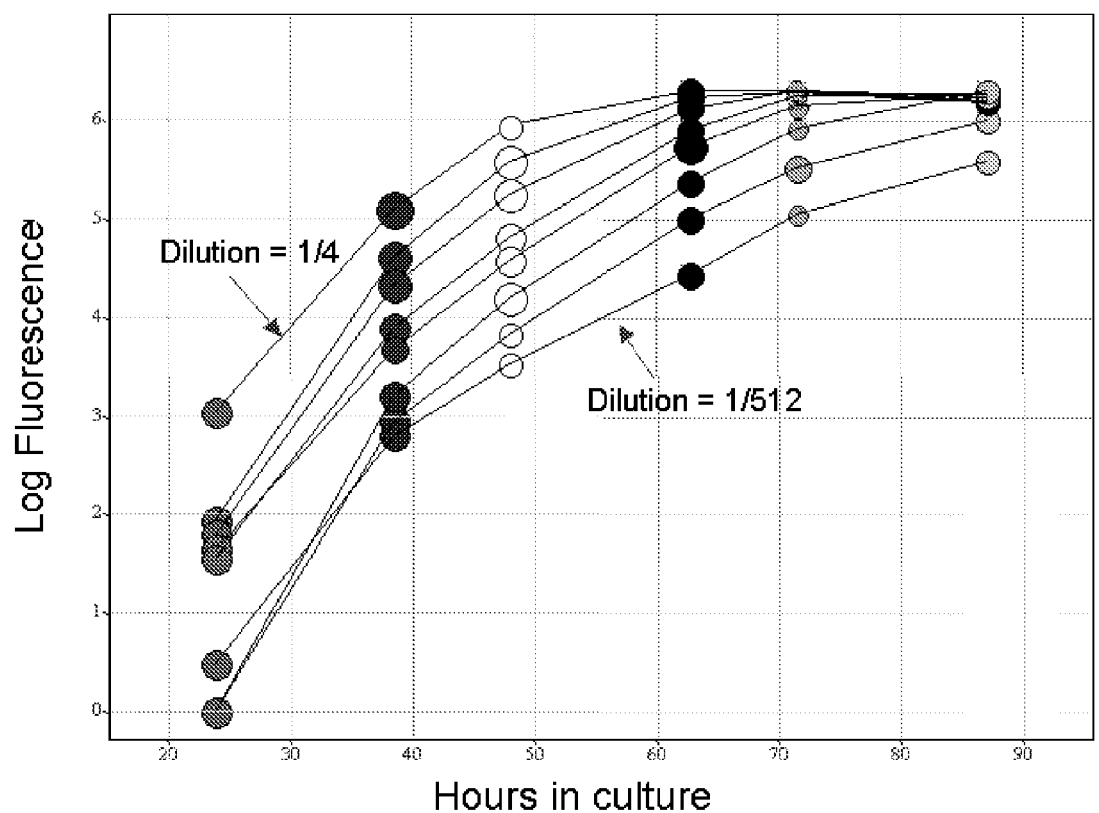
FIG. 2 depicts the growth curve of the HIV-1 wild-type virus IIIB at dilutions 1/4, 1/8, 1/16, 1/32, 1/64, 1/128, 1/256, and 1/512.

In a first embodiment, the invention relates to a method for the determination of the replication rate of a viral population, said method comprising the steps of:
a) diluting the viral population into at least 2 different dilutions;
b) providing cells into wells, wherein the amount of wells is the amount of the different dilutions from step a) in duplicate, triplicate or any other multiple;
c) infecting the multiple wells of cells with each dilution of the viral population so as to promote the replication of said viral population, wherein said cells or viral population comprise a phenotypic marker, whose signal is proportional to the logarithm of the viral population count;
d) measuring in a suitable device for each well the signal expressed by the phenotypic marker at least 2 different time points;
e) calculating a weight (w) for each group of signals of the wells with the same dilution at each time point (dilution multiple set), whereby said weight is a monotone decreasing function of the standard deviation of the signals;
f) plotting the logarithm of the signal data obtained from step d), in function of the time, and disregarding the signal data which is outside the linear region;
g) extrapolating each remaining signal data by adding said each remaining signal data to the logarithm of each dilution factor at which the viral population was diluted;
h) calculating the replication rate by performing a linear regression on the extrapolated remaining signal data and their corresponding time points; wherein the replication rate of the viral population (RR) is calculated according to the formula:

$$RR = \frac{\sum_{i=1}^{n} w_i x_i y_i - \frac{\sum_{i=1}^{n} w_i x_i \sum_{i=1}^{n} w_i y_i}{\sum_{i=1}^{n} w_i}}{\sum_{i=1}^{n} w_i x_i^2 - \frac{\left(\sum_{i=1}^{n} w_i x_i\right)^2}{\sum_{i=1}^{n} w_i}},$$

wherein "w" is the weight for each signal data set, "x" is a time point, "y" is each signal data for a given time point multiplied by the dilution factor, and "n" is the total number of signal data.

The term "replication" refers to the process in which a complementary strand of a nucleic acid molecule is synthesized by a polymerase enzyme. In the particular context of the present invention, the term replication as used herein in reference to a virus, refers to the completion of a complete or entire viral life cycle, wherein infectious viral particles or virions attach to the surface of the host cell (usually binding to a specific cell surface molecule that accounts for the specificity of the infection). Once inside the cell, the virions are uncoated and viral genes begin to express leading to the synthesis of proteins needed for replication of the genome and synthesis of new proteins to make new capsids and cores leading to the assembly of progeny infectious virus particles which, themselves, are capable of infecting and replicating in new host cells. Thus, a viral life cycle is only complete if, within a single cell, infection by one or more virus particles or virions proceeds all the way to the production of fully infectious progeny virus particles.

In the particular case of retroviruses, a complete viral life cycle involves infectious viral particles containing the viral RNA entering a cell, the RNA being reverse transcribed into DNA, the DNA being integrated into the host chromosome as a provirus, and the infected cell producing virion proteins and assembling them with full length viral genomic RNA into new, equally infectious particles.

The term "replication rate" refers to the factor by which the viral population grows, and is the slope of the line resulting from the linear regression performed in step h) of the method of the present invention. The term "replication rate" also refers to the increase or drop in viral population count; and/or to the percentage of virus replication relative to a reference virus strain, usually a wild-type strain such as IIIB or NL4-3. The wild-type strain is the reference virus from which the existence of mutations is based.

The term "viral population" refers to any sample comprising at least one virus, or a collection of virus particles. A sample may be obtained for example from an individual plant or animal, preferably a mammal, from cell cultures, or generated using recombinant technology, or cloning. The virus particles of the viral population may all be of the same species and strain, or they may be a mixed population.

One embodiment of the present invention relates to a viral population which comprises a population of recombinant or randomly mutagenized particles, for example retroviral particles. A viral population can comprise multiple virus carrying variations of one or more gene coding sequences.

In one embodiment of the invention, the viral population includes viruses known to infect mammals, including dogs, cats, horses, sheep, cows etc. In a preferred embodiment, the viruses are known to infect primates. In an even more preferred embodiment the viruses are known to infect humans. HIV strains compatible with the present invention are any such strains that are capable of infecting mammals, particularly humans.

Examples of human viruses include, but are not limited to, HIV, in particular HIV-1, and HIV-2, SIV, herpes simplex virus, cytomegalovirus virus, varicella poster virus, other human herpes viruses, influenza A virus, respiratory syncytial virus, hepatitis A, B and C viruses, rhinovirus, and human papilloma virus. The foregoing are representative of certain viruses for which there is presently available antiviral chemotherapy and represent the viral families retroviridae, herpesviridae, orthomyxoviridae, paramxyxovirus, picornavirus, flavivirus, pneumovirus and hepadnaviridae. Preferably the viral population comprises HIV, thus any HIV including laboratory strains, wild type strains, mutant strains and any biological sample comprising at least one HIV virus, such as, for example, an HIV clinical isolate. This invention can as well be used with other viral infections due to other viruses within these families as well as viral infections arising from viruses in other viral families.

HIV strains compatible with the present invention are any such strains that are capable of infecting cell lines and humans. Viral strains used for obtaining a plasmid are preferably HIV wild-type sequences, such as LAI, IIIB, HXB2D for HIV subtype B studies. Other clones of HIV from other subtypes or groups may also be used.

In another embodiment, the viral population may be obtained from a culture. In some embodiments, the culture can be obtained from a laboratory. In other embodiments, the culture can be obtained from a collection, for example, the American Type Culture Collection. In certain embodiments, the viral population comprises the derivative of a virus. In one embodiment, the derivative of the virus is not itself pathogenic. In some embodiments, the derivative of the virus comprises the nucleic acids or proteins of interest, for example, those nucleic acids or proteins to be targeted by an antiviral treatment. In one embodiment, the genes of interest can be incorporated into a vector. In a preferred embodiment, the genes can be those that encode for a protease or reverse transcriptase.

In another embodiment, the intact virus in a viral population need not be used. Instead, a part of the virus incorporated into a vector can be used. Preferably that part of the virus is used that is targeted by an antiviral drug.

In another embodiment, the viral population comprises a genetically modified virus. The virus can be genetically modified using any method known in the art for genetically modifying a virus. For example, the virus can be grown for a desired number of generations in a laboratory culture. In one embodiment, no selective pressure is applied (i.e., the virus is not subjected to a treatment that favors the replication of viruses with certain characteristics), and new mutations accumulate through random genetic drift. In another embodiment, a selective pressure is applied to the virus as it is grown in culture (i.e., the virus is grown under conditions that favor the replication of viruses having one or more characteristics). In one embodiment, the selective pressure is an antiviral treatment. Any known antiviral treatment can be used as the selective pressure.

In one embodiment, the virus is HIV and the selective pressure is a compound having antiretroviral activity such as suramine, pentamidine, thymopentin, castanospermine, dextran (dextran sulfate), foscarnet-sodium (trisodium phosphono formate); nucleoside reverse transcriptase inhibitors (NRTIs), e.g. zidovudine (AZT), didanosine (ddI), zalcitabine (ddC), lamivudine (3TC), stavudine (d4T), emtricitabine (FTC), abacavir (ABC), D-D4FC (Reverset™), alovudine (MIV-310), amdoxovir (DAPD), elvucitabine (ACH-126,443), and the like; non-nucleoside reverse transcriptase inhibitors (NNRTIs) such as delarvidine (DLV), efavirenz (EFV), nevirapine (NVP), capravirine (CPV), calanolide A, TMC120, etravirine (TMC125), TMC278, BMS-561390, DPC-083 and the like; nucleotide reverse transcriptase inhibitors (NtRTIs), e.g. tenofovir (TDF) and tenofovir disoproxil fumarate, and the like; compounds of the TIBO (tetrahydroimidazo[4,5,1-jk][1,4]-benzodiazepine-2(1H)-one and thione)-type e.g. (S)-8-chloro-4,5,6,7-tetrahydro-5-methyl-6-(3-methyl-2-butenyl)imidazo-[4,5,1-jk][1,4]benzodiazepine-2(1H)-thione; compounds of the α-APA (α-anilino phenyl acetamide) type e.g. α-[(2-nitrophenyl)amino]-2,6-dichlorobenzene-acetamide and the like; inhibitors of trans-activating proteins, such as TAT-inhibitors, e.g. RO-5-3335; REV inhibitors; protease inhibitors e.g. ritonavir (RTV), saquinavir (SQV), lopinavir (ABT-378 or LPV), indinavir (IDV), amprenavir (VX-478), TMC-126, BMS-232632, VX-175, DMP-323, DMP-450 (Mozenavir), nelfinavir (AG-1343), atazanavir (BMS 232,632), palinavir, TMC-114, RO033-4649, fosamprenavir (GW433908 or VX-175), P-1946, BMS 186,318, SC-55389a, L-756,423, tipranavir (PNU-140690), BILA 1096 BS, U-140690, and the like; entry inhibitors which comprise fusion inhibitors (e.g. T-20, T-1249), attachment inhibitors and co-receptor inhibitors; the latter comprise the CCRS antagonists and CXR4 antagonists (e.g. AMD-3100); examples of entry inhibitors are enfuvirtide (ENF), GSK-873,140, PRO-542, SCH-417,690, TNX-355, maraviroc (UK-427,857); gag processing inhibitors (or maturation inhibitors) such as PA-457 (Panacos Pharmaceuticals); inhibitors of the viral integrase; ribonucleotide reductase inhibitors (cellular inhibitors), e.g. hydroxyurea and the like; capsid protein polymerization inhibitors; budding inhibitors or assembly inhibitors.

By treating HIV cultured in vitro with one or more NNRTI, NRTI, PI or other antiretroviral drugs, one can select for mutant strains of HIV that have an increased resistance to these drugs respectively. The stringency of the selective pressure can be manipulated to increase or decrease the survival of viruses not having the selected-for characteristic.

In another aspect, the viral population comprises mutagenized virus, a viral genome, or a part of a viral genome. Any method of mutagenesis known in the art can be used for this purpose. In one embodiment, the mutagenesis is essentially random. In another embodiment, the essentially random mutagenesis is performed by exposing the virus, viral genome or part of the viral genome to a mutagenic treatment. In another embodiment, a gene that encodes a viral protein that is the target of an antiviral therapy is mutagenized. Examples of essentially random mutagenic treatments include, for example, exposure to mutagenic substances (e.g. ethidium bromide, ethylmethane-sulphonate, ethyl nitroso urea (ENU) etc.), radiation (e.g. ultraviolet light), the insertion and/or removal of transposable elements (e.g. TnS, Talc), or replication in a cell, cell extract, or in vitro replication system that has an increased rate of mutagenesis. See e.g. Russell et al., 1979, Proc. Nat. Acad. Sci. USA 76:5918-5922; Russell, W., 1982, 20 Environmental Mutagens and Carcinogens: Proceedings of The Third International Conference on Environmental Mutagens. One of skill in the art will appreciate that while each of these methods of mutagenesis is essentially random, at a molecular level, each has its own preferred targets.

In another aspect, the viral population comprises virus which have undergone a site-directed mutagenesis. Any method of site-directed mutagenesis known in the art can be used (see e.g., Sambrook et al., 2001, Molecular Cloning: A Laboratory Manual, Cold Spring Harbor Laboratory, 3rd ea., NY; and Ausubel et al., 1989, Current Protocols in Molecular Biology, Greene Publishing Associates and Wiley Interscience, NY). The site directed mutagenesis can be directed to, e.g., a particular gene or genomic region, a particular part of a gene or genomic region, or one or a few particular nucleotides within a gene or genomic region. In one embodiment, the site directed mutagenesis is directed to a viral genomic region, gene, gene fragment, or nucleotide based on one or more criteria. In one embodiment, a gene or a portion of a gene is subjected to site-directed mutagenesis because it encodes a protein that is known or suspected to be a target of an antiviral therapy, e.g. the gene encoding the HIV reverse transcriptase, protease, integrase or envelope. In another embodiment, a portion of a gene, or one or a few nucleotides within a gene, are selected for site-directed mutagenesis. In one embodiment, the nucleotides to be mutagenized encode amino acid residues that are known or suspected to interact with an antiviral compound. In another embodiment, the nucleotides to be mutagenized encode amino acid residues that are known or suspected to be mutated in viral strains having an impaired replication rate. In another embodiment, the mutagenized nucleotides encode amino acid residues that are adjacent to or near in the primary sequence of the protein residues known or suspected to interact with an antiviral compound or known or suspected to be mutated in viral strains having an impaired replication rate. In another embodiment, the mutagenized nucleotides encode amino acid residues that are adjacent to or near to in the secondary, tertiary or quaternary structure of the protein residues known or suspected to interact with an antiviral compound or known or suspected to be mutated in viral strains having an impaired replication rate. In another embodiment, the mutagenized nucleotides encode amino acid residues in or near the active site of a protein that is known or suspected to bind to an antiviral compound. See e.g. Sarkar and Sommer, 1990, Biotechniques, 8:404-407.

Usually the methods of the present invention are carried out on viral population extracted from a subject. A "subject" may be any organism, particularly a human or other mammal, suffering from a viral disease, or in need or desire of treatment for such disease. A subject includes any mammal and particularly humans of any age or state of development.

To obtain a viral population from a subject, a biological sample is obtained from the subject. A "biological sample" may be any material obtained in a direct or indirect way from a subject infected with a virus. A biological sample may be obtained from, for example, saliva, semen, breast milk, blood, plasma, faeces, urine, tissue samples, mucous samples, cells in cell culture, cells which may be further cultured, etc. Biological samples also include tissue and biopsy samples.

In one embodiment of the present invention, the viral population is provided in a viral stock solution. Several methods are known to the skilled in the art to prepare infectious HIV-1 virus stocks. One way is by infection of PHA-stimulated normal donor peripheral blood mononuclear cells (PBMC) with infectious culture supernatant. Tipically, HIV-1 virus stocks are obtained from cell cultures infected with the viral population, wherein the cells are centrifuged and the supernatant comprising the viral population is taken, mixed and diluted if required. Thus, culture supernatants, containing the virus are aliquoted and stored at around −65° C. to −85° C. until further processing, and in liquid nitrogen ($N_2$) for long term storage.

The dilution of the viral population into at least 2 different dilutions means that a viral population as defined hereinabove is mixed with two or more different volumes of medium thereby becoming diluted into 2 or more different dilutions, e.g.:

- a same volume of virus is mixed with the same volume of medium (dilution 1/2), and a same volume of virus is mixed with 2 times the volume of medium (dilution 1/3), thereby obtaining 2 different dilutions; or
- a same volume of virus is mixed with the same volume of medium (dilution 1/2), and a same volume of virus is mixed with 2 times the volume of medium (dilution 1/3), and a same volume of virus is mixed with 3 times the volume of medium (dilution 1/4), thereby obtaining 3 different dilutions; or
- a same volume of virus is mixed with the same volume of medium (dilution 1/2), and a same volume of virus is mixed with 2 times the volume of medium (dilution 1/3), and a same volume of virus is mixed with 3 times the volume of medium (dilution 1/4), and a same volume of virus is mixed with 4 times the volume of medium (dilution 1/5), thereby obtaining 4 different dilutions; etc.

Medium used in the invention refers to a cell-culture medium as defined herein below.

Preferably, dilutions are performed in series, meaning that a starting dilution is further diluted in subsequent dilutions following the same factor of dilution. As such dilution series may be one-fold, two-fold, three-fold, four-fold etc. Two-fold dilution refers to the series of different dilutions 1, 1/2, 1/4, 1/8, 1/16, 1/32, 1/64, 1/128, 1/256, etc. Three-fold dilution refers to the series of different dilutions 1, 1/3, 1/9, 1/27, 1/81, 1/243, etc.

In practice, in a two-fold dilution, a starting specific volume of a viral population is admixed with the same volume of medium thereby obtaining dilution 1/2. Then, a specific volume of dilution 1/2 is taken and admixed with a same volume of medium thereby obtaining dilution and so on. In the context of this series, "1" refers to the starting viral population sample, "1/2" refers to a dilution wherein 1 part of a viral population sample is admixed with 1 part of medium, "1/4" refers to a dilution wherein 1 part of the 1/2 dilution sample is admixed with 1 part of medium, "1/8" refers to a dilution wherein 1 part of the 1/4 dilution sample is admixed with 1 part of medium, "1/16" refers to a dilution wherein 1 part of the 1/8 dilution sample is admixed with 1 part of medium, "1/32" refers to a dilution wherein 1 part of the 1/16 dilution sample is admixed with 1 part of medium, "1/64" refers to a dilution wherein 1 part of the 1/32 dilution sample is admixed with 1 part of medium, "1/128" refers to a dilution wherein 1 part of the 1/64 dilution sample is admixed with 1 part of medium, "1/256" refers to a dilution wherein 1 part of the 1/128 dilution sample is admixed with 1 part of medium, and so on.

In one embodiment of the present invention, virus stock solutions are serially diluted in a series of 3, 4, 5, 6, 7, or 8 different dilutions (for instance 1/4, 1/8, 1/16, 1/32, 1/64, 1/128, 1/256, 1/512) and used to infect HIV susceptible cell lines equipped with a phenotypic marker.

The dilution exercise can be easily automated in a pipetting apparatus employing appropriate plasticware such as microtiter plates. Dilutions are usually performed on any container suitable for virus. Plasticware is preferable including tubes, vials, plates and microtiterplates. Microtiterplates allow for an automated dilution exercise.

The term "wells" in the passage "providing cells into wells" refers to any type of container suitable for the storage and testing of cells and virus. As such, wells refers to any type of labware containers, such as vials, tubes, plates and microtiter plates. Preferably the containers are plasticware. Microtiter plates may comprise for instance 6, 24, 96, 384, or 1536 wells.

The amount of wells is the amount of the different dilutions from step a) in duplicate, triplicate or any other multiple. This refers to the fact that a same volume of cells is placed in sets of two, three, four, or more wells. According to the method of the invention, there are as many sets as there are different dilutions performed in step a). Thus, and without being limited to the following exemplification, if, for instance, two different dilutions are performed in step a), there is provided 2 sets of wells with cells, wherein each set consists of, for example, 2 wells. In another example, three different dilutions are performed in step a), and there is provided 3 sets of wells with cells, wherein each set consists of, for example, 4 wells One embodiment of the present invention, involves the performance of two different dilutions in step a), and the provision of 2 sets of wells with cells, wherein each set consists of 3 wells. One embodiment of the present invention, involves the performance of two different dilutions in step a), and the provision of 2 sets of wells with cells, wherein each set consists of 4 wells.

One embodiment of the present invention, involves the performance of three different dilutions in step a), and the provision of 3 sets of wells with cells, wherein each set consists of 2 wells. One embodiment of the present invention, involves the performance of three different dilutions in step a), and the provision of 3 sets of wells with cells, wherein each set consists of 3 wells. One embodiment of the present invention, involves the performance of three different dilutions in step a), and the provision of 3 sets of wells with cells, wherein each set consists of 4 wells.

One embodiment of the present invention, involves the performance of four different dilutions in step a), and the provision of 4 sets of wells with cells, wherein each set consists of 2 wells. One embodiment of the present invention, involves the performance of four different dilutions in step a), and the provision of 4 sets of wells with cells, wherein each set consists of 3 wells. One embodiment of the present invention, involves the performance of four different dilutions in step a), and the provision of 4 sets of wells with cells, wherein each set consists of 4 wells.

One embodiment of the present invention, involves the performance of five different dilutions in step a), and the provision of 5 sets of wells with cells, wherein each set consists of 2 wells. One embodiment of the present invention, involves the performance of five different dilutions in step a), and the provision of 5 sets of wells with cells, wherein each set consists of 3 wells. One embodiment of the present invention, involves the performance of five different dilutions in step a), and the provision of 5 sets of wells with cells, wherein each set consists of 4 wells.

One embodiment of the present invention, involves the performance of six different dilutions in step a), and the provision of 6 sets of wells with cells, wherein each set consists of 2 wells. One embodiment of the present invention, involves the performance of six different dilutions in step a), and the provision of 6 sets of wells with cells, wherein each set consists of 3 wells. One embodiment of the present invention, involves the performance of six different dilutions in step a), and the provision of 6 sets of wells with cells, wherein each set consists of 4 wells.

One embodiment of the present invention, involves the performance of seven different dilutions in step a), and the provision of 7 sets of wells with cells, wherein each set consists of 2 wells. One embodiment of the present invention, involves the performance of seven different dilutions in step a), and the provision of 7 sets of wells with cells, wherein each set consists of 3 wells. One embodiment of the present invention, involves the performance of seven different dilutions in step a), and the provision of 7 sets of wells with cells, wherein each set consists of 4 wells.

One embodiment of the present invention, involves the performance of eight different dilutions in step a), and the provision of 8 sets of wells with cells, wherein each set consists of 2 wells. One embodiment of the present invention, involves the performance of eight different dilutions in step a), and the provision of 8 sets of wells with cells, wherein each set consists of 3 wells. One embodiment of the present invention, involves the performance of eight different dilutions in step a), and the provision of 8 sets of wells with cells, wherein each set consists of 4 wells.

The provision of cells in sets of wells for each dilution improves the accuracy of the method of the present invention. By having repeats of a same experiment, a weight can be calculated and applied for each signal data set into the linear regression formula of the present invention.

Infecting cells so as to promote the replication of said viral population refers to the invasion of cells by the viral population. The person skilled in the art is acquainted with the methodologies to promote in vitro infection. Typically, the cells and virus are incubated, usually in a $CO_2$ atmosphere, to promote infection.

Monitoring the infection of the cells may be performed by different methods known to the skilled in the art. One common methodology is the visual follow-up of the cytopathogenic effect (CPE) which is usually performed with a microscope.

Promoting replication refers to the provision of the suitable conditions for the virus to be able to infect cells and thereby producing new virion copies. Said conditions include the incubation of the cell culture with the viral population at beneficial temperatures in a $CO_2$ atmosphere. Other conditions include the provision of a suitable humidity, food, and for instance the absence of any antiviral which can jeopardize the replication of a virus. Alternatively, "promoting replication" may as well be performed in specific conditions, such as the presence of specific antivirals to study the effect thereof on a given viral population. Alternatively, said conditions include environmental factors, such as and without being limited to, competitive binding proteins such as albumin, $\alpha 1$-glycoprotein, different types of cell lines, etc.

Where the virus is HIV, the cells may be chosen from T cells, monocytes, macrophages, dendritic cells, Langerhans cells, hematopoietic stem cells, peripheral blood mononuclear cells (PBMC) or, precursor cells, human T-lymphoblastoid cell lines, like MT4, MT2, CEM, and PM-1 cells. Cells are usually CD4+ T leukocytes and any sub-family thereof. Preferably, the cell line susceptible to infection by HIV is a CD4+ T-cell line. Further, preferably, the CD4+ T-cell line is the MT4 cell line or the HeLa CD4+ cell line.

There are many varied types of cell culture media that can be used to support cell viability, for example DMEM medium (H. J. Morton, In Vitro, 6, 89/1970), F12 medium (R. G. Ham, Proc. Natl. Acad. Sci. USA, 53, 288/1965) and RPI 1640 medium (J. W. Goding, J. Immunol. Methods, 39, 285/1980, JAMA 199, 519/1957). Such media is usually supplemented with a nutritional content required by most animal cells. Typical supplements include fetal bovine serum (FBS), horse serum or human serum, used in significant concentrations. An example of a protein-rich medium is RPMI1640 supplemented with fetal calf serum at 10%, L-glutamine, and antibiotics such as penicillin, and streptomycin. Interestingly, prior to HIV infection, PBMCs may be stimulated with phytohemagglutinin for some days and maintained in R-20 medium (RPMI 1640 supplemented with fetal calf serum), L-glutamine, HEPES buffer, recombinant human interleukin-2; penicillin, and streptomycin.

Cells may as well be maintained in a serum-free medium, whereby the cell culture medium consists of media, purified lipoprotein material; and optionally a reduced concentration of serum, such as fetal bovine serum (FBS). The terms "cell culture medium", "culture medium" and "medium formulation" refer to a nutritive solution for culturing or growing cells. A "serum-free" medium is a medium that contains no serum (e.g., fetal bovine serum (FBS), horse serum, goat serum, or any other animal-derived serum known to one skilled in the art). Examples of "serum-free" medium are provided in WO05/070120.

The cells will be thus preferably available in a cell culture. The specific culture conditions will depend on the cells used and, if present in the cells, the phenotypic markers to be produced and their expression systems. The process of culturing cells is generally divided into two phases, a preliminary phase where the cells start growing, and a subsequent phase where the cells continue to grow at a controlled rate determined by various parameters, such as pH, dissolved oxygen, ethanol concentration, carbon source (e.g., glucose) concentration, temperature, culture biomass and growth rate, and the like. Monitoring changes in one or more of these parameters, which may be performed by standard instrumentation, provides feedback for maintaining the proper growth rate of the cell culture.

Appropriate cell densities will depend on the characteristics of the specific host cells utilized. Thus, densities of viable cells for carrying out the present invention may vary from $10^3$ cells/ml to $10^8$ cells/ml preferably around $10^4$ cells/ml, $10^5$ cells/ml, $1.5\times10^5$ cells/ml, or $10^6$ cells/ml. Usually, a cell population is continuously grown from a single cell or inoculum of lower viable cell density in a cell culture medium in a constant or increasing culture volume. Concentration of a cell culture or suspension will be usually achieved by centrifugation of the cells into a cell pellet and removal of the supernatant. The required volume of medium is added to the cell pellet. This may be done as many times as needed.

A phenotypic marker is an observable biochemical structure, molecule, function, or behavior associated with a cell, tissue, organism, or individual. Examples of phenotypes include the physical parts, macromolecules, cell-surface proteins, metabolism, and behaviors of a cell, tissue, organism, or individual.

Reporter genes encode an activity, such as, but not limited to, production of RNA, peptide, or protein, or can provide a binding site for RNA, peptides, proteins, inorganic and organic compounds or compositions and the like. Reporter genes are therefore suitable means for providing a phenotypic marker. For example, reporter genes may encode for any enzyme that is necessary for cell growth, or one encoding a protein detectable by a colorimetric assay or one whose expression leads to a loss of color.

Examples of reporter genes include but are not limited to: (1) nucleic acid segments that encode products which provide resistance against otherwise toxic compounds (e.g., antibiotics); (2) nucleic acid segments that encode products which are otherwise lacking in the recipient cell (e.g., tRNA genes, auxotrophic markers); (3) nucleic acid segments that encode products which suppress the activity of a gene product; (4) nucleic acid segments that encode products which can be readily identified (e.g., phenotypic markers such as β-galactosidase, green fluorescent protein (GFP), yellow fluorescent protein (YFP), cyan fluorescent protein (CFP), and cell surface proteins); (5) nucleic acid segments that bind products which are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g. restriction endonucleases); (8) nucleic acid segments that can be used to isolate or identify a desired molecule (e.g. specific protein binding sites); (9) nucleic acid segments that encode a specific nucleotide sequence which can be otherwise non-functional (e.g., for PCR amplification of subpopulations of molecules); and/or (10) nucleic acid segments, which when absent, directly or indirectly confer resistance or sensitivity to particular compounds.

Particularly preferred reporter genes are those encoding fluorescent markers, such as the GFP gene and variants thereof. Reporter genes may facilitate either a selection or a screen for reporter gene expression, and quantitative differences in reporter gene expression may be measured as an indication of interaction affinities. Examples of reporter genes include β-galactosidase, green fluorescent protein (GFP), yellow fluorescent protein (YFP), cyan fluorescent protein (CFP), red fluorescent protein (DsRed2), and cell surface proteins.

Other phenotypic markers are known in the art and can be used in this invention. In one embodiment of the present invention, the cells encompass a reporter gene, preferably inserted in the cellular DNA.

Viral population count is the number of individual RNA copies. Another equivalent term is "viral load". The number of RNA copies can be calculated according to different methodologies known to the skilled in the art, and commercially available kits known to the skilled in the art.

As a consequence of plotting the logarithm of the signal data in function of the time, the signal expressed by the phenotypic marker and produced by the instrument needs to be proportional to the logarithm of the viral population count. One of skill in the art will also understand that the method of the present invention may also be applied with signal data which is plotted in function of the time in a non-logarithmic domain, for instance in a linear domain. As such, then the signal data needs to be proportional to the viral population count, whereby the replication rate is calculated according to the following formula:

$$RR = \frac{\sum_{i=1}^{n} w_i x_i \log y_i - \dfrac{\sum_{i=1}^{n} w_i x_i \sum_{i=1}^{n} w_i \log y_i}{\sum_{i=1}^{n} w_i}}{\sum_{i=1}^{n} w_i x_i^2 - \dfrac{\left(\sum_{i=1}^{n} w_i x_i\right)^2}{\sum_{i=1}^{n} w_i}}$$

The handling of the data will thus be adapted to the type of instrument used for reading the signal expressed by the phenotypic markers.

Suitable devices for measuring the signal expressed by a phenotypic marker will obviously depend on the phenotypic marker. As such, in the case of a green fluorescence protein, the suitable device will be any apparatus able to measure fluorescence.

Measuring at least 2 different time points refers to the measurement of the mixture of cells and virus at two different times, three different times, four different times, etc. Preferably the signal expressed by the phenotypic marker is measured at 3 different time points. Also preferably the signal expressed by the phenotypic marker is measured at 4 different time points. Also preferably the signal expressed by the phenotypic marker is measured at 5 different time points. Also preferably the signal expressed by the phenotypic marker is measured at 6 different time points. Also preferably the signal expressed by the phenotypic marker is measured at 7 different time points, for instance, the signal expressed by the phenotypic marker may be measured at 2 or more of the times such as at 0 h, 24 h, 39 h, 48 h, 63 h, 72 h and 87 h. Other time schedules are also possible. 0 (zero) hours refers to the moment when the viral population is admixed with the cells. Usually, the wells containing the mixture are placed in an incubator under suitable conditions. After a desirable amount of time, the content of the wells are evaluated by measuring the phenotypic marker signal using a suitable detector, and subsequently the wells are placed back in the incubator. This is performed as many times as there are time points needed.

For illustration purposes, the method of the present invention, in a limited embodiment, consists of:

Given 2 different dilutions of the viral population:
Dilution A: which is 1 volume of the viral population admixed with 1 volume of medium; i.e. 1/2
Dilution B: which is 1 volume of the viral population admixed with 3 volumes of medium; i.e. 1/4

A suspension of cells is then distributed in for instance 8 individual wells, 4 wells for dilution A and 4 wells for dilution B. Then, dilution A is added to each of 4 wells having the same cell culture; and dilution B is added to each of the remaining 4 wells having as well the same cell culture.

The wells with the cells and virus are maintained in suitable conditions. At a given moment, all 8 wells are read in a device. After for instance 12 hours, the same 8 wells are read again. These readings shall provide 16 signal data, i.e. one value per well at time a hours and one value per well at time 13 (a+12 hours).

| Material | Value at time α | Value at time β (α + 12 hours) |
|---|---|---|
| A1 | A1α | A1β |
| A2 | A2α | A2β |
| A3 | A3α | A3β |
| A4 | A4α | A4β |
| B1 | B1α | B1β |
| B2 | B2α | B2β |
| B3 | B3α | B3β |
| B4 | B4α | B4β |

The calculation of a weight for each group of signals of the wells with the same dilution at each time point, is performed for each dilution multiple set, i.e. a weight is calculated for each of the following set of values:

| | |
|---|---|
| A1α, A2α, A3α, and A4α; | wAα |
| B1α, B2α, B3α, and B4α; | wBα |
| A1β, A2β, A3β, and A4β; | wAβ |
| B1β, B2β, B3β, and B4β. | wBβ |

The weight is calculated by applying a monotone decreasing function of the standard deviation of the dilution multiple set. Thus, first the standard deviation is calculated for each set of values. The monotone decreasing function refers to a function which reverses the order of the standard deviation. In a preferred embodiment, the weight is calculated according to the formula:

$$w=1/(SD+F),$$

wherein "SD" is the standard deviation in the log domain for each dilution multiple set, and "F" is a constant. Constant "F" may be any number, preferably smaller than 1, for example and without being limited 0.05, 0.03, or 0.01.

In a preferred embodiment of the present invention, each dilution multiple set within which those extreme values are more than 1-log apart from each other, is disregarded.

Subsequently, the logarithm of the values or signal data obtained are plotted in function of the time, and the signal data which is outside the linear region is disregarded. In one embodiment of the present invention, the $\log_{10}$ of the fluorescence signal data which is smaller or higher than the detection limits of the measuring device is disregarded. In a preferred embodiment of the present invention, the cells are equipped with the phenotypic marker GFP and the signal data which is smaller than 3.0 and higher than 6.0 is disregarded.

For each remaining signal data, there is added the logarithm of each dilution factor at which the viral population was diluted. By this addition, the signal data is extrapolated as if the viral concentration was the same in all of the wells. If the method of the present invention is to be applied in the normal domain (thus not in the log domain), the dilution factor will be multiplied to the remaining signal data, instead of being added the logarithm thereof.

Then, the replication rate is calculated by performing a linear regression on the extrapolated remaining signal data and their corresponding time points; wherein the replication rate of the viral population (RR) is calculated according to the formula:

$$RR = \frac{\sum_{i=1}^{n} w_i x_i y_i - \frac{\sum_{i=1}^{n} w_i x_i \sum_{i=1}^{n} w_i y_i}{\sum_{i=1}^{n} w_i}}{\sum_{i=1}^{n} w_i x_i^2 - \frac{\left(\sum_{i=1}^{n} w_i x_i\right)^2}{\sum_{i=1}^{n} w_i}},$$

wherein "w" is the weight for each signal data set, "x" is a time point, "y" is each signal data for a given time point multiplied by the dilution factor, and "n" is the total number of signal data.

In the present invention the linear regression analyzes the relationship between the two variables, the time point (x), and the signal data for a given point multiplied by its the dilution factor (y). A third variable, "w", i.e. the weight for each signal data set, increases the accuracy of the present method by increasing or decreasing the influence of the signal data sets according to their level of variation.

Linear regression finds the line that minimizes the sum of the squares of the vertical distances of the points from the line. More precisely, the goal of regression is to minimize the sum of the squares of the vertical distances of the points from the line.

The slope quantifies the steepness of the line. It equals the change in "y" for each unit change in "x". It is expressed in the units of the "y"-axis divided by the units of the "x"-axis. If the slope is positive, "y" increases as "x" increases. If the slope is negative, "y" decreases as "x" increases. In the present invention, the slope represents the replication rate. The "y" intercept is the "y" value of the line when "x" equals zero. It defines the elevation of the line.

In one embodiment of the present invention, the signal expressed by the phenotypic marker is measured at more than 2 time points, e.g., the measurements for a same sample are performed at time points α, β, γ, δ, ε, and ζ, and more if desirable. In such scenario, a linear regression may be performed for each two, three, four or more consecutive signal data and their corresponding time points. The skilled in the art will understand that the amount of consecutive signal data and their corresponding time points shall depend on the size of the linear region, i.e. the bigger the linear region is, the more consecutive signal data that may be considered. Preferably, the linear regression is performed for each two consecutive signal data and their corresponding time points. More preferably, the linear regression is performed for each three consecutive signal data and their corresponding time points.

Thus, when the measurements for a same sample are performed at time points α, β, γ, δ, ε, and ζ, and the linear regression is performed for each two consecutive signal data and their corresponding time points, 5 linear regressions will be possible, one linear regression between values at time points α and β; another linear regression between values at time points β and γ; another linear regression between values at time points γ and δ; another linear regression between values at time points δ and ε; and another linear regression between values at time points ε and ζ. Obviously, five slopes will be obtained and the greatest slope will be the replication rate.

In one preferable embodiment of the present invention, the linear regression is performed for each three consecutive signal data and their corresponding time points. The performance of the linear regression on three consecutive signal data and their corresponding time points increases the robustness of the methodology. Thus, in the scenario where the measurements for a same sample are performed at time points α, β, γ, δ, ε, and ζ, 4 linear regressions will be possible, one linear regression between values at time points α, β and γ; another linear regression between values at time points β, γ, and δ; another linear regression between values at time points γ, δ, and ε; and another linear regression between values at time points δ, ε, and ζ. Obviously, four slopes will be obtained and the greatest slope will be the replication rate.

In one embodiment of the present invention, the replication rate is expressed as an increase or a drop in viral population count between 2 time points. In a preferred embodiment of the present invention, the replication rate is expressed as an increase or a drop in viral population count between 3 time points.

In one embodiment of the present invention, the replication rate is expressed as the factor by which the viral population grows by calculating the inverse logarithm of the obtained greatest slope.

In one embodiment of the present invention, the replication rate is calculated for a given viral population and for a reference viral population, and the replication rate of said given viral population is divided by the replication rate of the reference viral population, and the replication rate of said given viral population is expressed in a percentage relative to the replication rate of the reference viral population. This approach allows a rapid comparison between different viral populations.

In one embodiment of the present invention, the reference viral population consists of wild-type virus. In another embodiment of the present invention, the reference viral population consists of specific mutant virus strains.

The methods according to the present invention may be used as a diagnostic method for predicting disease progression exhibited by a particular viral population with which a patient is infected. According to other preferred embodiments, the method may be used for assessing the efficiency of a patient's therapy or for evaluating or optimizing a therapy. The method may be performed for each drug or combination of drugs currently being administered to the patient to assess the effect of a plurality of drugs or drug combinations on the calculated replicated rate exhibited by the viral population with which the patient is infected.

The term "therapy" includes but is not limited to a drug, pharmaceutical, or any other compound or combination of compounds that can be used in therapy or therapeutic treatment of a virus, in particular HIV.

The invention further relates to a diagnostic system as herein described for use in any of the methods described herein. An example of such a diagnostic system, for determining the replication rate of a viral population, comprises:

a) means for diluting a viral population;

b) means for providing cells into wells;

c) means for infecting cells so as to promote the replication of said viral population, wherein said cells or viral population comprise a phenotypic marker, the measurement of which is proportional to the logarithm of the viral population count;

d) means for measuring the signal expressed by the phenotypic marker;

e) means for calculating the replication rate using any one of the methods described herein.

The means for diluting a viral population comprise pipettes, tips, preferably disposable tips, suitable plasticware, virus stocks, media, and cells. The means for providing cells into wells comprise pipettes, tips, preferably disposable tips, suitable plasticware, preferably microtiter plates, media, cells. Preferably the means for diluting a viral population and the means for providing cells into wells include an automated pipetting station.

The means for infecting cells so as to promote the replication of said viral population, involve means for bringing the cells into contact with the viral population, such as pipettes, tips, preferably disposable tips, suitable plasticware, preferably microtiter plates, virus stocks, media, and cells; and means for conditioning the mixture of cells and virus, such as an incubator at suitable amounts of $CO_2$, temperature, humidity, and nutrients, such as medium, serum, and the like.

The means for measuring the signal expressed by the phenotypic marker include any suitable analytical detection device, such as fluorimeters, colorimeters, spectrographs, and the like.

The means for calculating the replication rate are preferably computer means.

A still further aspect of the invention relates to a computer apparatus or computer-based system adapted to perform any one of the methods of the invention described herein, for example, to calculate the replication rate of a given viral population. Such computer apparatus or computer-based system is characterised in that it is adapted by means of computer programs to convert the input signal data, time points and dilution factors to a replication rate using steps e)-h) of the method of the invention, namely by:

i) calculating a weight (w) for each group of signals of the wells with the same dilution at each time point (dilution multiple set), whereby said weight is a monotone decreasing function of the standard deviation of the signals;

j) plotting the logarithm of the signal data obtained from step d), in function of the time, and disregarding the signal data which is outside the linear region;

k) extrapolating each remaining signal data by adding said each remaining signal data to the logarithm of each dilution factor at which the viral population was diluted;

l) calculating the replication rate by performing a linear regression on the extrapolated remaining signal data and their corresponding time points; wherein the replication rate of the viral population (RR) is calculated according to the formula:

$$RR = \frac{\sum_{i=1}^{n} w_i x_i y_i - \frac{\sum_{i=1}^{n} w_i x_i \sum_{i=1}^{n} w_i y_i}{\sum_{i=1}^{n} w_i}}{\sum_{i=1}^{n} w_i x_i^2 - \frac{\left(\sum_{i=1}^{n} w_i x_i\right)^2}{\sum_{i=1}^{n} w_i}},$$

wherein "w" is the weight for each signal data set, "x" is a time point, "y" is each signal data for a given time point multiplied by the dilution factor, and "n" is the total number of signal data.

In a preferred embodiment of the invention, said computer apparatus may comprise a processor means incorporating a memory means adapted for storing data; means for inputting data relating to the signal expressed by the phenotypic marker of each of the multiple different dilutions of the viral population, and the dilution factors; and computer software means stored in said computer memory that is adapted to perform a method according to any one of the embodiments of the invention described herein and output a replication rate for a viral population.

A computer system of this aspect of the invention may comprise a central processing unit; an input device for inputting requests; an output device; a memory; and at least one bus connecting the central processing unit, the memory, the input device and the output device. The memory should store a module that is configured so that upon receiving a request to calculate the replication rate of a viral population, it performs the steps listed in any one of the methods of the invention described herein.

In the apparatus and systems of these embodiments of the invention, data may be input by downloading the signal data expressed by the phenotypic marker from a local site such as a memory or disk drive, or alternatively from a remote site accessed over a network such as the internet. The signal data and/or the dilution factors may be input by keyboard, if required.

The generated results may be output in any convenient format, for example, to a printer, a word processing program, a graphics viewing program or to a screen display device. Other convenient formats will be apparent to the skilled reader.

The means adapted to determine the replication rate of a viral population will preferably comprise computer software means. As the skilled reader will appreciate, once the novel and inventive teaching of the invention is appreciated, any number of different computer software means may be designed to implement this teaching.

According to a still further aspect of the invention, there is provided a computer program product for use in conjunction with a computer, said computer program comprising a computer readable storage medium and a computer program mechanism embedded therein, the computer program mechanism comprising a module that is configured so that upon receiving a request to calculate the replication rate of a viral population, it performs the steps listed in any one of the methods of the invention described herein.

The invention further relates to systems, computer program products, business methods, server side and client side systems and methods for generating, providing, and transmitting the results of the above methods.

The invention will now be described by way of example with particular reference to a specific algorithm that implements the process of the invention. As the skilled reader will appreciate, variations from this specific illustrated embodiment are of course possible without departing from the scope of the invention.

Example

A 384-well plate was filled as displayed in FIG. 1.
The 384-well plate encompassed:
32 wells with cells (columns 1 & 2) which were the cell's negative control
32 wells with wild-type virus IIIB (columns 3 & 4), which was diluted into eight different dilutions (1/4, 1/8, 1/16, 1/32, 1/64, 1/128, 1/256, and 1/512). Each dilution was applied in quadruplicates. These 32 wells with the wild-type virus IIIB were the positive controls of the experiment.
32 wells for each of the virus V1, V2, V3, V4, V5, V6, V7, V8, V9 in columns 5 & 6, 7 & 8, 9 & 10, 11 & 12, 13 & 14, 15 & 16, 17 & 18, 19 & 20, and 21 & 22, respectively having the same set-up as the wild-type virus wells.
16 wells with medium (wells A23 to H23 & wells A24 to H24) which were the medium's negative control
16 wells with cells (wells I23 to P23 & wells I24 to P24) which were also the cell's negative control The wells of columns 1 and 2, wells 23I to 23P, and wells 24I to 24P contained 200 µl of MT4 cells equipped with a fluorescence marker at a concentration of 500,000 cells/ml. The wells 23A to 23H, and wells 24H to 24I contained 200 µl of medium. Each of the remaining wells contained 100 µl of the virus in the specific dilution and 100 µl of re-suspended MT4 cells at a concentration of 500,000 cells/ml.

The 384-well plate was then placed in the incubator at 37° C. and the time was annotated as 0 hour (h). The plate was then read in a laser at 6 time points between 24 and 86 hours after placement in the incubator, i.e., at 24 h, 39 h, 48 h, 63 h, 72 h and 87 h.

Once the fluorescence data was obtained from all the 6 time points, the $\log_{10}$ of the fluorescence data was plotted against the time in culture (hours). See FIG. 2 which depicts the growth curve of the HIV-1 wild-type virus IIIB at dilutions 1/4, 1/8, 1/16, 1/32, 1/64, 1/128, 1/256, and 1/512.

Figure 3:
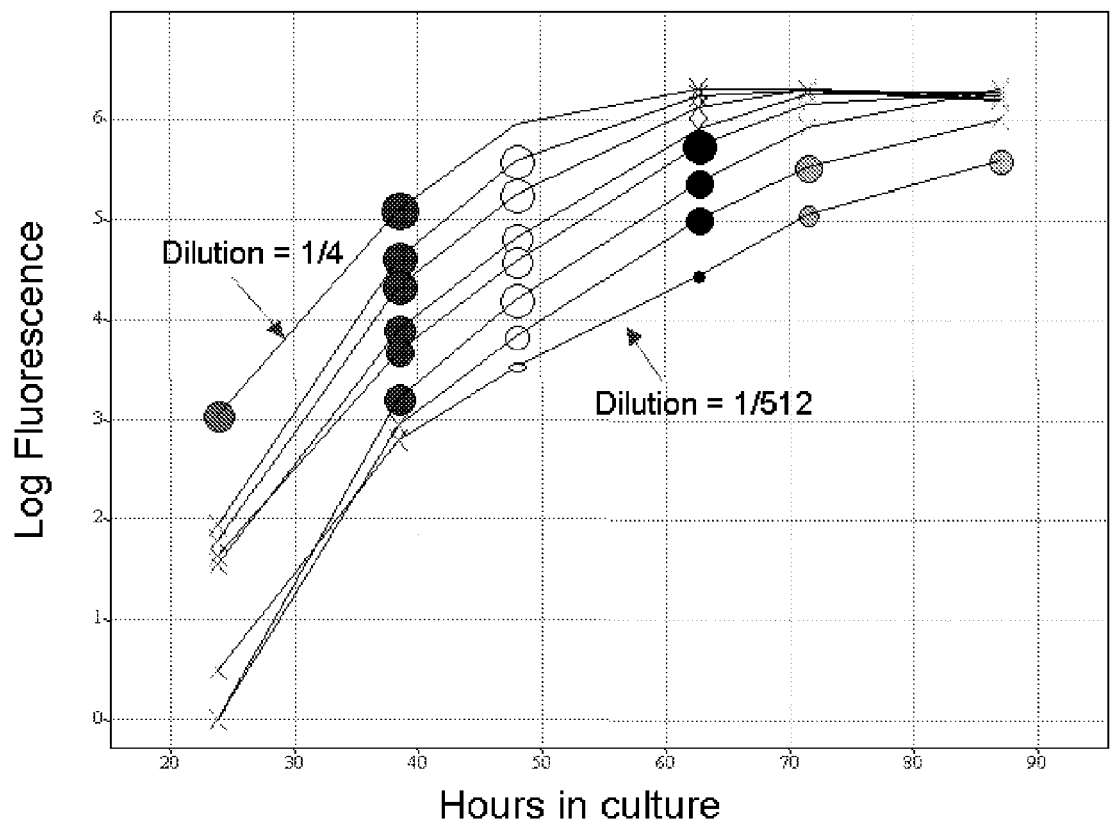
FIG. 3 depicts the growth curve of the HIV-1 wild-type virus IIIB at dilutions 1/4, 1/8, 1/16, 1/32, 1/64, 1/128, 1/256, and 1/512, wherein the restriction criterion is applied and the values outside the range 3-5.5 are shown as crosses (X).

The following restriction criterion was applied to the data:
The $\log_{10}$ of the fluorescence values must be between 3.0 and 5.5 to 6.0 (depending of the detection device). As such, the $\log_{10}$ of the fluorescence values outside the range of 3.0-5.5 were disregarded. In FIG. 3, the values outside the range are shown as crosses (X).

The standard deviation for each raw data quadruplicate was calculated (in the log domain) and a "weight" was assigned to each average time point according to the formula:

$$W = 1/(SD+0.03)$$

Figure 4:
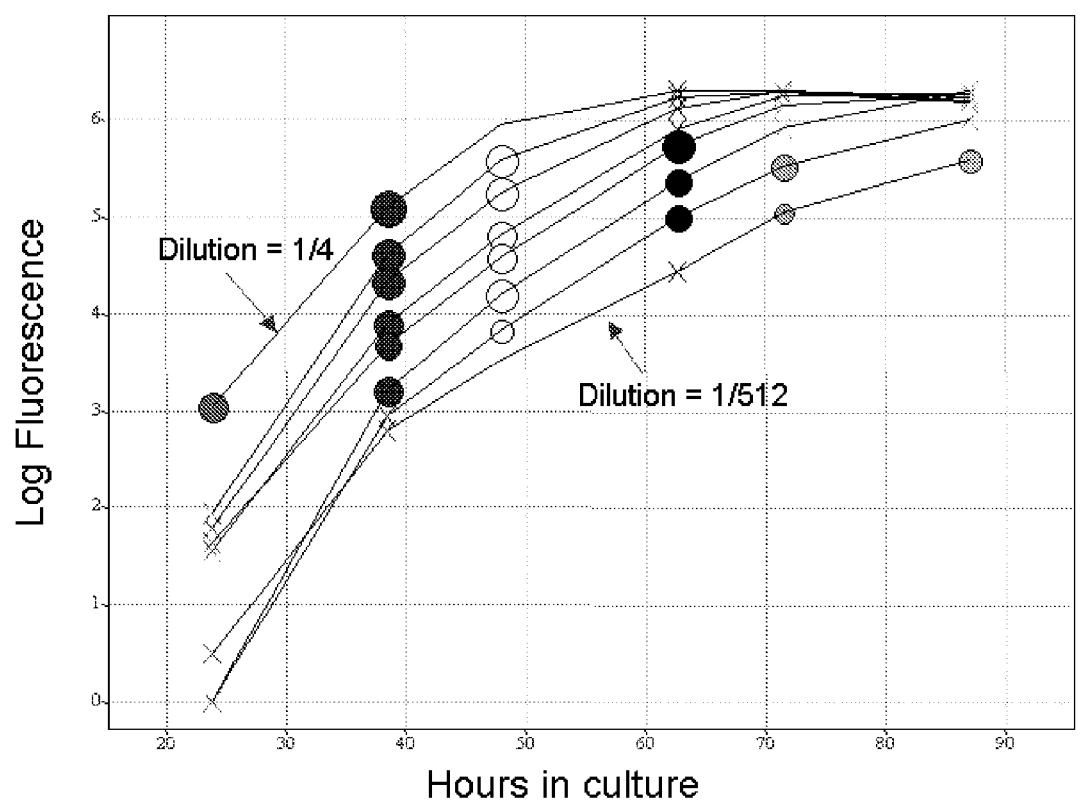
FIG. 4 depicts the growth curve of the HIV-1 wild-type virus IIIB at dilutions 1/4, 1/8, 1/16, 1/32, 1/64, 1/128, 1/256, and 1/512, wherein the extreme values for each raw data quadruplicate which are more than 1-log apart, are shown as crosses (X).

When the extreme values for each raw data quadruplicate were more than one-log apart, the data point was removed. In FIG. 4, the values removed are shown as crosses (X).

The fluorescence data was extrapolated as if the viral concentration was the same in all the 384-well plates. This was achieved by multiplying the fluorescence (F) by the viral dilution ($D_V$).

$$F \times D_V = F_P$$

In the log domain, the formula transformed in the addition of the $\log_{10}$ of the fluorescence and the $\log_{10}$ of the dilution.

$$\log_{10} F + \log_{10} D_V = \log_{10} F_P$$

The extrapolated fluorescence is a function of time (t) due to the viral growth $\text{Log}_{10} F_P = f(t)$, where $F_P$ is the extrapolated fluorescence.

Figure 5:
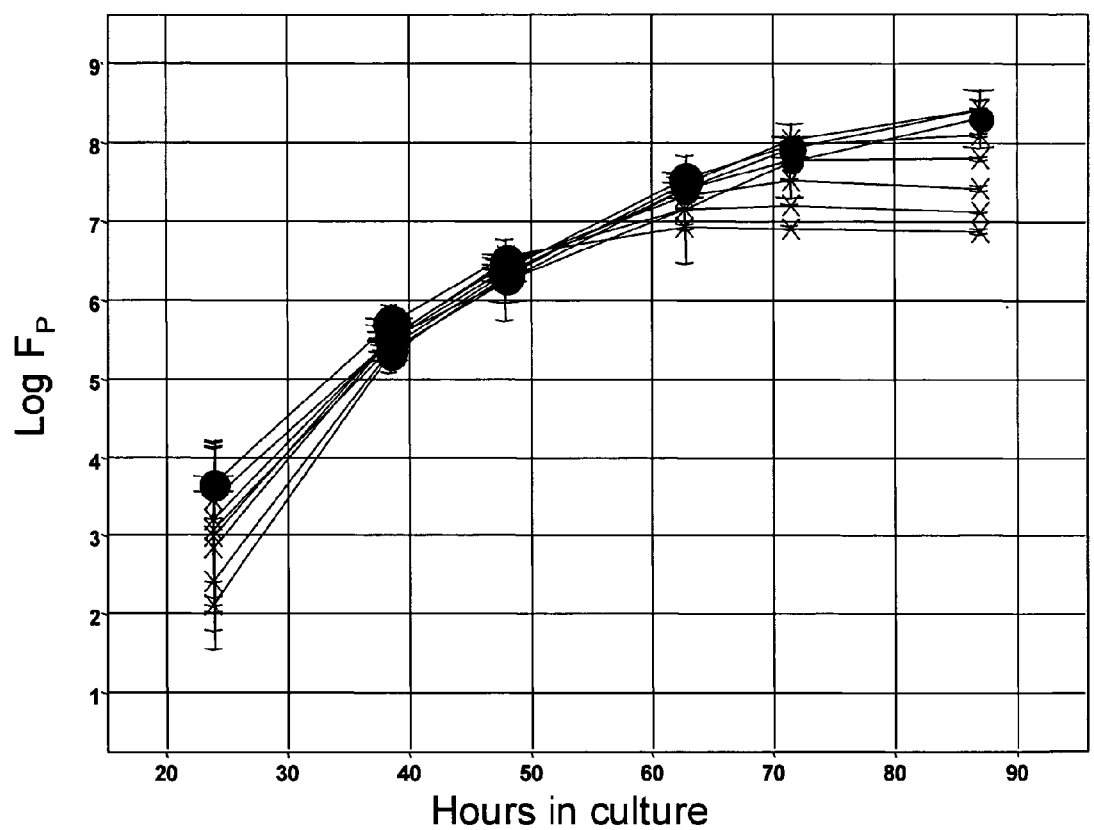
FIG. 5 depicts the extrapolated growth curves of HIV-1 IIIB at different dilutions (in the log domain).

In FIG. 5, the extrapolated growth curves of HIV-1 IIIB at different dilutions (in the log domain) were depicted.

The replication rate was then calculated by performing a linear regression on the extrapolated remaining signal data and their corresponding time points; and replication rate was calculated according to the formula:

$$RR = \frac{\sum_{i=1}^{n} w_i x_i y_i - \frac{\sum_{i=1}^{n} w_i x_i \sum_{i=1}^{n} w_i y_i}{\sum_{i=1}^{n} w_i}}{\sum_{i=1}^{n} w_i x_i^2 - \frac{\left(\sum_{i=1}^{n} w_i x_i\right)^2}{\sum_{i=1}^{n} w_i}},$$

wherein "w" is the weight for each signal data set, "x" is a time point, "y" is each signal data for a given time point multiplied by the dilution factor, and "n" is the total number of signal data.

Figure 6:
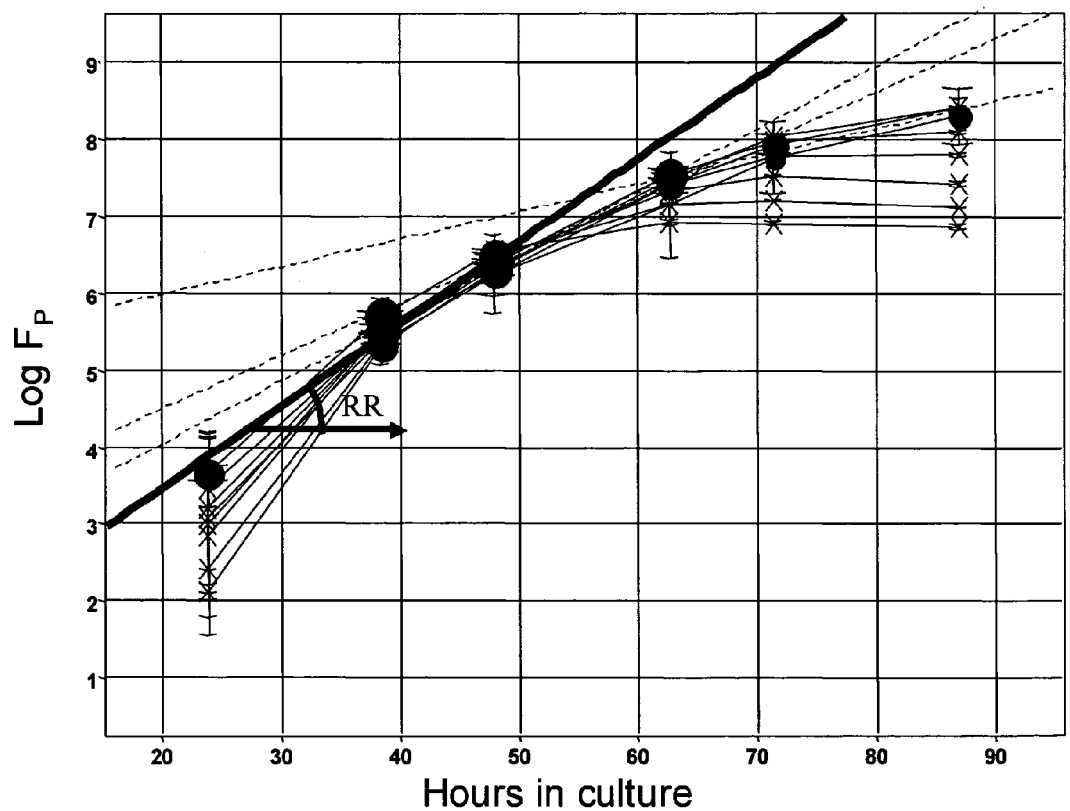
FIG. 6 depicts the extrapolated growth curves of HIV-1 IIIB at different dilutions (in the log domain), wherein the linear regressions are also plotted, the one with greatest inclination is shown in bold.

Since different lines were possible, the line with the greatest inclination was taken, whereby its slope was the replication rate. In FIG. 6, different linear regressions are plotted, the one with greatest inclination is shown in bold.

Figure 7:
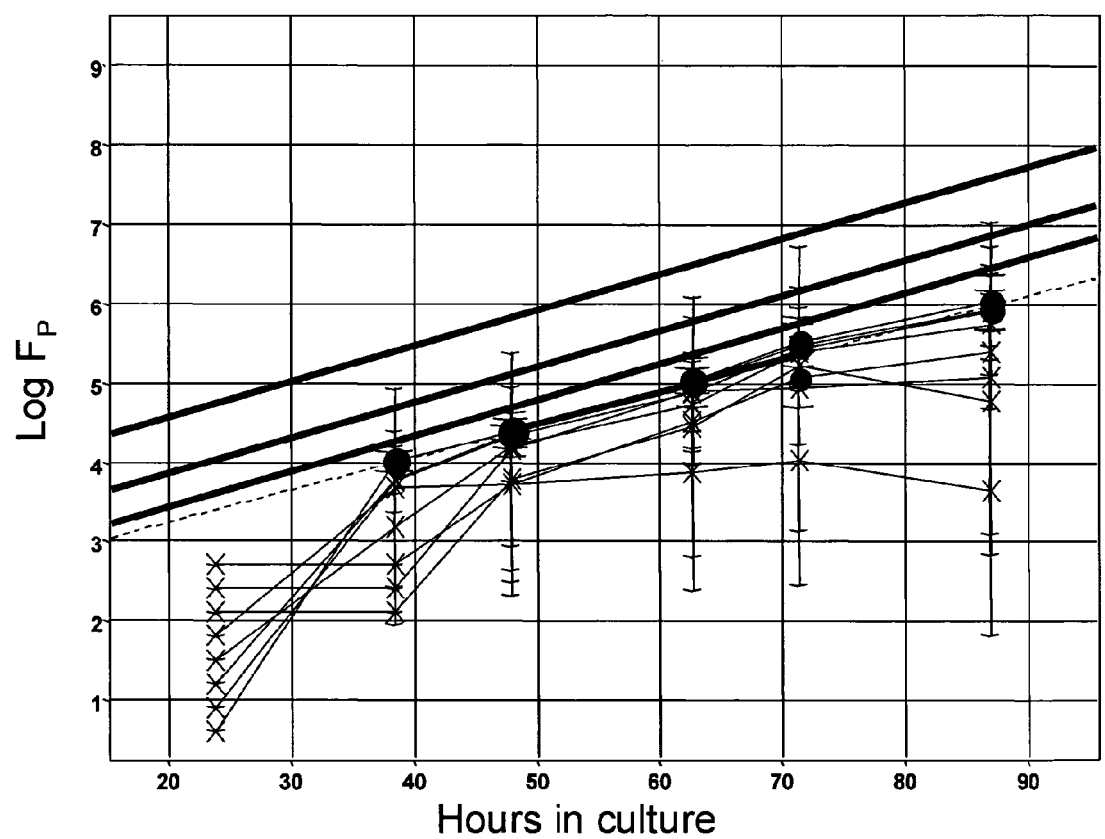
FIG. 7 depicts the reproducibility of the method according to the present invention which was run 4 different times with the same virus strain (T20908).

In FIG. 7, there is plotted 4 different experiments according to the present invention which were run with the same virus strain (T20908). The linear regression obtained clearly show the reproducibility of the method.

Figure 8:
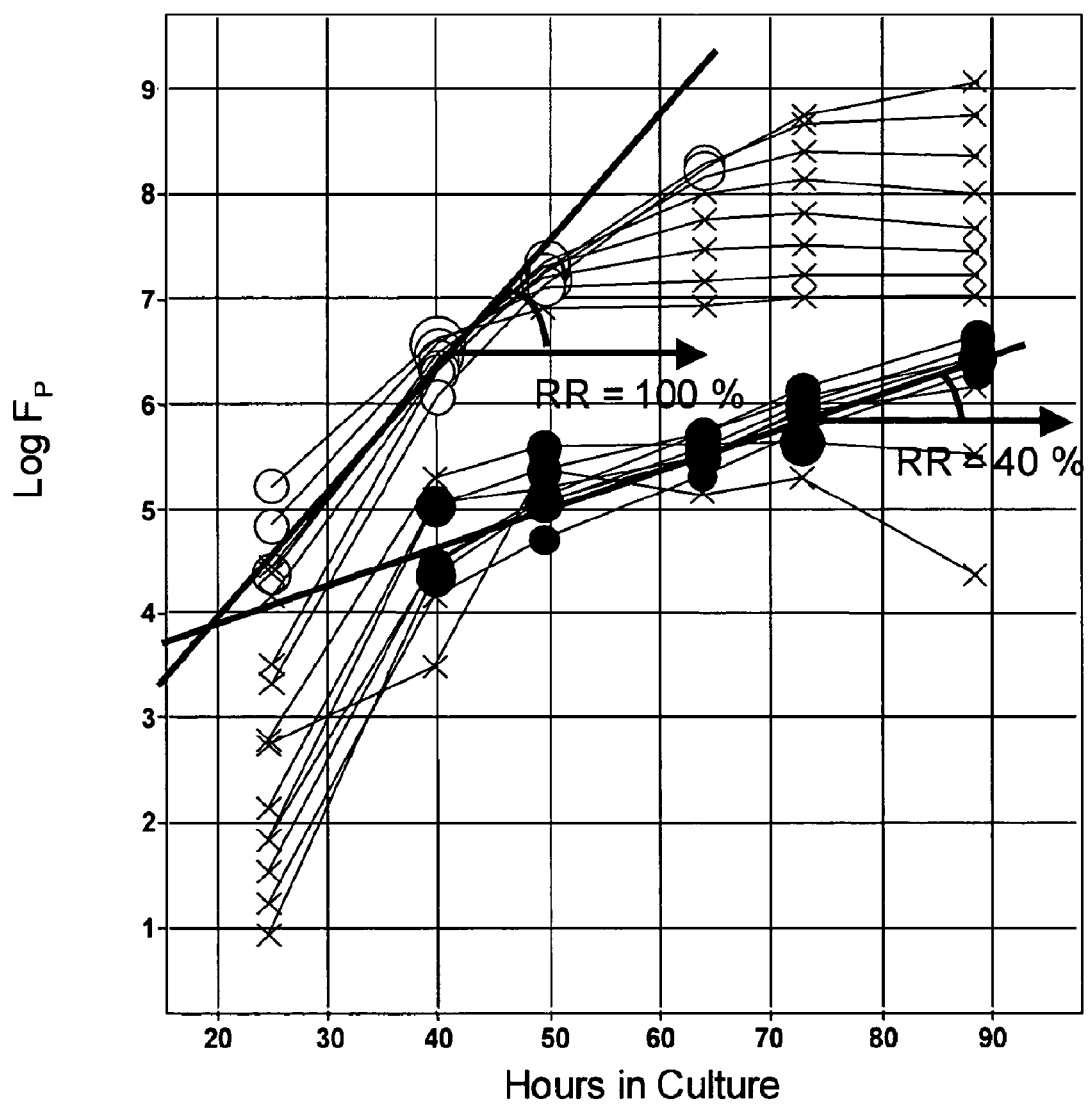
FIG. 8 depicts the replication rate of virus 1 expressed in a percentage (RR=40%) relative to the replication rate of the wild-type virus IIIB (RR=100%).

In FIG. 8, the replication rate of virus 1 is expressed in a percentage (RR=40%) relative to the replication rate of the wild-type virus IIIB (RR=100%).

The invention claimed is:

1. A method for determining a replication rate of a viral population, said method comprising the steps of:
   a) diluting the viral population into at least 2 different dilutions;
   b) providing cells into wells, wherein the amount of wells is the amount of the different dilutions from step a) in duplicate, triplicate or any other multiple;
   c) infecting the multiple wells of cells with each dilution of the viral population so as to promote replication of said viral population, wherein said cells or viral population comprise a phenotypic marker, whose signal is proportional to the logarithm of the viral population count;
   d) measuring in a suitable device for each well the signal expressed by the phenotypic marker for at least 2 different time points;
   e) calculating a weight (w) for each group of signals of the wells with the same dilution at each time point, wherein each group of signals of the wells with the same dilution at each time point is a dilution multiple set, whereby said weight is a monotone decreasing function of the standard deviation of the signals;
   f) plotting the logarithm of the signal data obtained from step d), in function of the time, and disregarding the signal data which is outside the linear region;
   g) extrapolating each remaining signal data by adding said each remaining signal data to the logarithm of each dilution factor at which the viral population was diluted; and
   h) calculating the replication rate by performing a linear regression on the extrapolated remaining signal data and their corresponding time points; wherein the replication rate of the viral population (RR) is calculated according to the formula:

$$RR = \frac{\sum_{i=1}^{n} w_i x_i y_i - \frac{\sum_{i=1}^{n} w_i x_i \sum_{i=1}^{n} w_i y_i}{\sum_{i=1}^{n} w_i}}{\sum_{i=1}^{n} w_i x_i^2 - \frac{\left(\sum_{i=1}^{n} w_i x_i\right)^2}{\sum_{i=1}^{n} w_i}},$$

wherein the replication of a viral population refers to the completion of an entire viral life cycle, "w" is the weight for each signal data set, "x" is a time point, "y" is each signal data for a given time point multiplied by the dilution factor, and "n" is the total number of signal data.

2. The method according to claim 1 wherein in step e) the weight (w) is calculated according to the formula:

$w=1/(SD+F)$, wherein "SD" is the standard deviation in the log domain for each dilution multiple set, and "F" is a constant.

3. The method according to any one of claims 1-2 wherein before step g), each dilution multiple set within which those extreme values are more than 1-log apart from each other, is disregarded.

4. The method according to claim 1 wherein the signal expressed by the phenotypic marker is measured at 5 time points, and 3 linear regressions are performed on each three consecutive signal data obtained from step g) and their corresponding time points, whereby the replication rate is the greatest slope obtained.

5. The method according to claim 1 wherein the signal expressed by the phenotypic marker is measured at 6 time points, and 4 linear regressions are performed on each three consecutive signal data obtained from step g) and their corresponding time points, whereby the replication rate is the greatest slope obtained.

6. The method according to claim 1 wherein the replication rate is expressed as the factor by which the viral population grows by calculating the inverse logarithm of the obtained greatest slope.

7. The method according to claim 1 wherein the replication rate is expressed as an increase or a drop in viral population count between 3 time points.

8. The method according to claim 1 wherein the replication rate is calculated for a given viral population and for a reference viral population, and the replication rate of said given viral population is divided by the replication rate of the reference viral population, and the replication rate of said given viral population is expressed in a percentage relative to the replication rate of the reference viral population.

9. The method according to claim 1 wherein the phenotypic marker is a reporter gene inserted in the cells.

10. The method according to claim 1 wherein the viral population consists of human immunodeficiency virus (HIV).

11. The method according to claim 1 further comprising assessing the efficiency of a subject's therapy or for evaluating or optimizing a therapy.

12. A computer apparatus or computer-based system comprising a memory for storing computer executable program instructions, and a processor operative to execute steps e)-h) of the method of claim 1 in response to the computer executable program instructions.

* * * * *